United States Patent
Kim et al.

(10) Patent No.: US 11,875,885 B2
(45) Date of Patent: *Jan. 16, 2024

(54) INTEROPERABLE PLATFORM FOR REDUCING REDUNDANCY IN MEDICAL DATABASE MANAGEMENT

(71) Applicant: BeiGene, Ltd., Grand Cayman (KY)

(72) Inventors: Geoffrey Kim, Ellicott City, MD (US); Bobby Y. Reddy, Boston, MA (US); Joel Choi Park, New York City, NY (US); Rajuli Lall, Lake Oswego, OR (US)

(73) Assignee: BEIGENE, LTD., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 18/191,195

(22) Filed: Mar. 28, 2023

(65) Prior Publication Data

US 2023/0245738 A1    Aug. 3, 2023

Related U.S. Application Data

(63) Continuation of application No. 17/804,763, filed on May 31, 2022, now Pat. No. 11,636,930, which is a
(Continued)

(51) Int. Cl.
*G16H 10/60* (2018.01)
*G16H 10/20* (2018.01)
(Continued)

(52) U.S. Cl.
CPC .......... *G16H 10/60* (2018.01); *G06F 16/248* (2019.01); *G06F 16/24573* (2019.01); *G16H 10/20* (2018.01); *G16H 15/00* (2018.01)

(58) Field of Classification Search
CPC ...... G16H 10/20; G16H 10/60; G06F 16/248; G06F 16/24573
(Continued)

(56) References Cited

U.S. PATENT DOCUMENTS 7,653,634 B2    1/2010  Mathur
8,073,710 B2    12/2011 Hasan et al.
(Continued)

FOREIGN PATENT DOCUMENTS

WO    WO2007084502 A1    7/2007
WO    WO-2014105752 A1 *  7/2014  ............. G16H 10/20
(Continued)

OTHER PUBLICATIONS

Teixeira, Pedro L., Jr.; Computational Phenotyping and Phenome-wide Association Studies: Leveraging Machine Learning and Natural Language Processing to Understand Electronic Health Record Data; Vanderbilt University. ProQuest Dissertations Publishing, 2015. 13835237. (Year: 2015).*

(Continued)

*Primary Examiner* — Hiep V Nguyen
(74) *Attorney, Agent, or Firm* — NORTON ROSE FULBRIGHT

(57) ABSTRACT

Systems and methods are disclosed for reducing redundancy in medical database management. An example system may include an application program interface communicatively linked to a user interface associated with each of: a plurality of hospital information systems, a plurality of source devices associated with each of the plurality of hospital information systems, and a plurality of electronic data management systems. The system may further include a mapping module configured to map lexical tokens between patient-specific data forms used by each of the system components. An example method may performed by a computing device having one or more processors may include receiving, from the source devices, patient-specific health data; generating updates to patient-specific electronic health records (EHR) for patients; generating patient-specific electronic data capture (EDC) data associated with the
(Continued)

patients, and updating electronic data management systems with the patient-specific EDC data.

20 Claims, 8 Drawing Sheets

Related U.S. Application Data continuation of application No. 17/374,223, filed on Jul. 13, 2021, now Pat. No. 11,393,566.

(51) Int. Cl.
*G06F 16/248* (2019.01)
*G06F 16/2457* (2019.01)
*G16H 15/00* (2018.01)

(58) Field of Classification Search
USPC .......................................................... 705/3
See application file for complete search history.

(56) References Cited

U.S. PATENT DOCUMENTS

| | | | |
|---|---|---|---|
| 8,606,593 | B1 | 12/2013 | Green, III |
| 8,626,533 | B2 | 1/2014 | Rao et al. |
| 8,850,057 | B2 | 9/2014 | Natoli et al. |
| 9,384,327 | B2 | 7/2016 | Snyder et al. |
| 9,824,185 | B2 | 11/2017 | Douglass et al. |
| 10,297,343 | B1 | 5/2019 | Wartenfeld et al. |
| 10,698,922 | B2 | 6/2020 | Bormann |
| 10,741,272 | B2 | 8/2020 | Venkat et al. |
| 10,878,010 | B2 | 12/2020 | Labkoff et al. |
| 10,878,064 | B2 | 12/2020 | Burns et al. |
| 10,892,046 | B1 | 1/2021 | Harding et al. |
| 11,048,704 | B2 | 6/2021 | Gunther |
| 2012/0271655 | A1 | 10/2012 | Knobel et al. |
| 2015/0351671 | A1 | 12/2015 | Vanslyke et al. |
| 2016/0070758 | A1 | 3/2016 | Thomson |
| 2017/0041296 | A1 | 2/2017 | Ford |
| 2019/0156958 | A1 | 5/2019 | Hartung et al. |
| 2019/0180862 | A1 | 6/2019 | Wisser et al. |
| 2019/0311791 | A1 | 10/2019 | St. Paul |
| 2020/0251225 | A1 | 8/2020 | Murrish et al. |
| 2021/0020294 | A1 | 1/2021 | Bharmi |
| 2021/0090694 | A1* | 3/2021 | Colley .................. G16H 50/70 |
| 2021/0225469 | A1 | 6/2021 | Valdes et al. |
| 2021/0313021 | A1* | 10/2021 | Rejndrup ............... G16H 40/67 |
| 2021/0350909 | A1 | 11/2021 | Saxena et al. |

FOREIGN PATENT DOCUMENTS

| | | | |
|---|---|---|---|
| WO | WO 2014105752 | A1 | 7/2014 |
| WO | WO-2015191562 | A1 * | 12/2015 ......... G06F 19/3418 |
| WO | WO2019230074 | A1 | 12/2019 |

OTHER PUBLICATIONS

Nordo, et al., Use of EHRs data for clinical research: Historical progress and current applications, Nov. 2019, Learning Health Systems, pp. 1-9. (Year: 2019). *.

Kolla, M. " Automatic text summarization using lexical chains: Algorithms and experiments", University of Lethbridge (Canada), *ProQuest Dissertations Publishing*, 2005.

* cited by examiner

INTEROPERABLE PLATFORM FOR REDUCING REDUNDANCY IN MEDICAL DATABASE MANAGEMENT

CROSS-REFERENCE TO RELATED APPLICATIONS

This application is a continuation of U.S. patent application Ser. No. 17/804,763, filed May 31, 2022, which is a continuation of U.S. patent application Ser. No. 17/374,223, filed Jul. 13, 2021 (now U.S. Pat. No. 11,393,566), the entire contents of each of the foregoing applications are incorporated herein by reference and relied upon.

BACKGROUND

Patient-specific medical data, obtained in hospitals, pharmacies, and/or via medical devices, are often relied on by a variety of different electronic database systems and servers and for a variety of end goals. For example, clinical research, development, and trials to overcome prevalent diseases often involve the large-scale capture of patient-specific data. Unfortunately, such patient-specific data capture often occurs in fragmented silos and/or in disparate settings, which lead to inconsistencies in the input of data. Moreover, patient-specific data captured at the disparate settings are often managed by different platforms and vendors, which may use different standards for entering medical data based on their respective end goals. Such standards (e.g., the format or syntax for entering medical data, required data fields, level of privacy or encryption, etc.) can often differ for patient-specific data captured for clinical trial research, billing and reimbursement, or medical record keeping. Thus, the same patient-specific data may need to be reentered, reformatted, and/or refined at different electronic data capture systems for different end goals. For instance, details regarding a patient's fever may need to be entered into an electronic medical record for the purpose of record keeping, a billing and claims form for the purpose of reimbursement, and an electronic data capture system for the purpose of clinical trials. Such fragmentation in medical data capture often contributes to inefficiencies in producing clinical data, suboptimal quality in the clinical data, and rising costs in research, development, and healthcare delivery. There is thus a desire for a seamless capture and transmission of patient-specific data that can be utilized by a plurality of medical data capture systems using a single data capture.

Various embodiments are presented herein that address one or more of these shortcomings.

SUMMARY

The present disclosure provides new and innovative systems and methods for reducing redundancy in medical database management. In an example, a method performed by a computing device having one or more processors may include performing one or more of the following steps for each of a plurality of hospital information systems, for each of a plurality of source devices associated with the plurality of hospital information systems, and for each of a plurality of patients: receiving, from a given source device associated with a given hospital information system, patient-specific health data for a given patient; generating, based on the patient-specific health data, an update to a patient-specific electronic health record (EHR) for the given patient; and generating, based on the patient-specific EHR, a patient-specific electronic data capture (EDC) data associated with the given patient. In some aspects, the generation of one form of patient-specific data (e.g., EDC data) from another form of patient-specific data (e.g., EHR) may occur by way of a mapping module that maps the structure, format, types, and preferred language of the original form to the new form. For example, lexical tokens may be mapped between a dictionary associated with the given hospital information system and a dictionary associated with the first electronic data management system.

The method may further include aggregating, in a first electronic data management system of a plurality of electronic data management systems, a plurality of patient-specific EDC data associated with the plurality of patients. In some aspects, the plurality of patient-specific EDC data may be generated from one or more iterations of the preceding steps. At predetermined refresh intervals, each of the plurality of electronic data management systems may be updated and/or synchronized to store the plurality of patient-specific EDC data associated with the plurality of patients.

In some aspects, the updating and/or synchronization of each of the plurality of electronic data management systems may include: receiving, from a second electronic data management system, an update to the patient-specific EDC data for a patient of the plurality of patients; and then updating, at a next occurrence of the predetermined refresh intervals, and based on the update to the patient-specific EDC data for the patient, the plurality of patient-specific EDC data at the remaining electronic data management systems of the plurality of electronic data management systems.

The method may further include identifying, based on a first tag associated with a subset of the plurality of patient-specific EDC data, a destination system for the subset of the plurality of patient-specific EDC data. The subset of the plurality of patient-specific EDC data may then be sent to the destination system. Moreover, the destination system may include for example, another hospital information system of the plurality of hospital information systems, or a second electronic data management system of the plurality of electronic data management systems.

In an example, a system for reducing redundancy in medical database management is disclosed. The system may include an application program interface (API) for reducing redundancy in medical database management and communicatively linked to a user interface associated with each of: a plurality of hospital information systems, a plurality of source devices associated with each of the plurality of hospital information systems, and a plurality of electronic data management systems. The system may further include a mapping module configured to map lexical tokens between the plurality of source devices, the plurality of hospital information systems, and the plurality of electronic data management systems. The system may further include memory and one or more processors in communication with the memory. The memory may store instructions that, when executed by the one or more processors, may cause the processor to performing one or more of the following steps for each of a plurality of hospital information systems, for each of a plurality of source devices associated with the plurality of hospital information systems, and for each of a plurality of patients: receiving, from a given source device associated with a given hospital information system, patient-specific health data for a given patient; generate, based on the patient-specific health data and using the mapping module, an update to a patient-specific electronic health record (EHR) for the given patient; and generate, using the mapping module and based on the patient-specific EHR, a patient-specific electronic data capture (EDC) data associated with the given patient.

The instructions, when executed, may further cause the processor to aggregate, in a first electronic data management system of a plurality of electronic data management systems, a plurality of patient-specific EDC data associated with the plurality of patients. In some aspects, the plurality of patient-specific EDC data may be generated from one or more iterations of the preceding steps. At predetermined refresh intervals, each of the plurality of electronic data management systems may be updated and/or synchronized to store the plurality of patient-specific EDC data associated with the plurality of patients.

In an example, a non-transitory computer-readable medium for use on a computer system is disclosed. The non-transitory computer-readable medium may contain computer-executable programming instructions may cause processors to perform a method for reducing redundancy in medical database management. The method may include performing one or more of the following steps for each of a plurality of hospital information systems, for each of a plurality of source devices associated with the plurality of hospital information systems, and for each of a plurality of patients: receiving, from a given source device associated with a given hospital information system, patient-specific health data for a given patient; generating, based on the patient-specific health data, an update to a patient-specific electronic health record (EHR) for the given patient; and generating, based on the patient-specific EHR, a patient-specific electronic data capture (EDC) data associated with the given patient.

The method may further include: sending, to a first electronic data management system of a plurality of electronic data management systems, and based on the generated patient-specific EDC data for each of the plurality of patients, a plurality of patient-specific EDC data associated with the plurality of patients; updating, at predetermined refresh intervals and using the first electronic data management system, each of the plurality of electronic data management systems to store the plurality of patient-specific EDC data associated with the plurality of patients; identifying, based on a first tag associated with a subset of the plurality of patient-specific EDC data, a destination system for the subset of the plurality of patient-specific EDC data; and sending, to the destination system, the subset of the plurality of patient-specific EDC data, wherein the destination system comprises one or more of (1) another hospital information system of the plurality of hospital information systems, or (2) a second electronic data management system of the plurality of electronic data management systems.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

DETAILED DESCRIPTION OF EXAMPLE EMBODIMENTS

Figure 1:
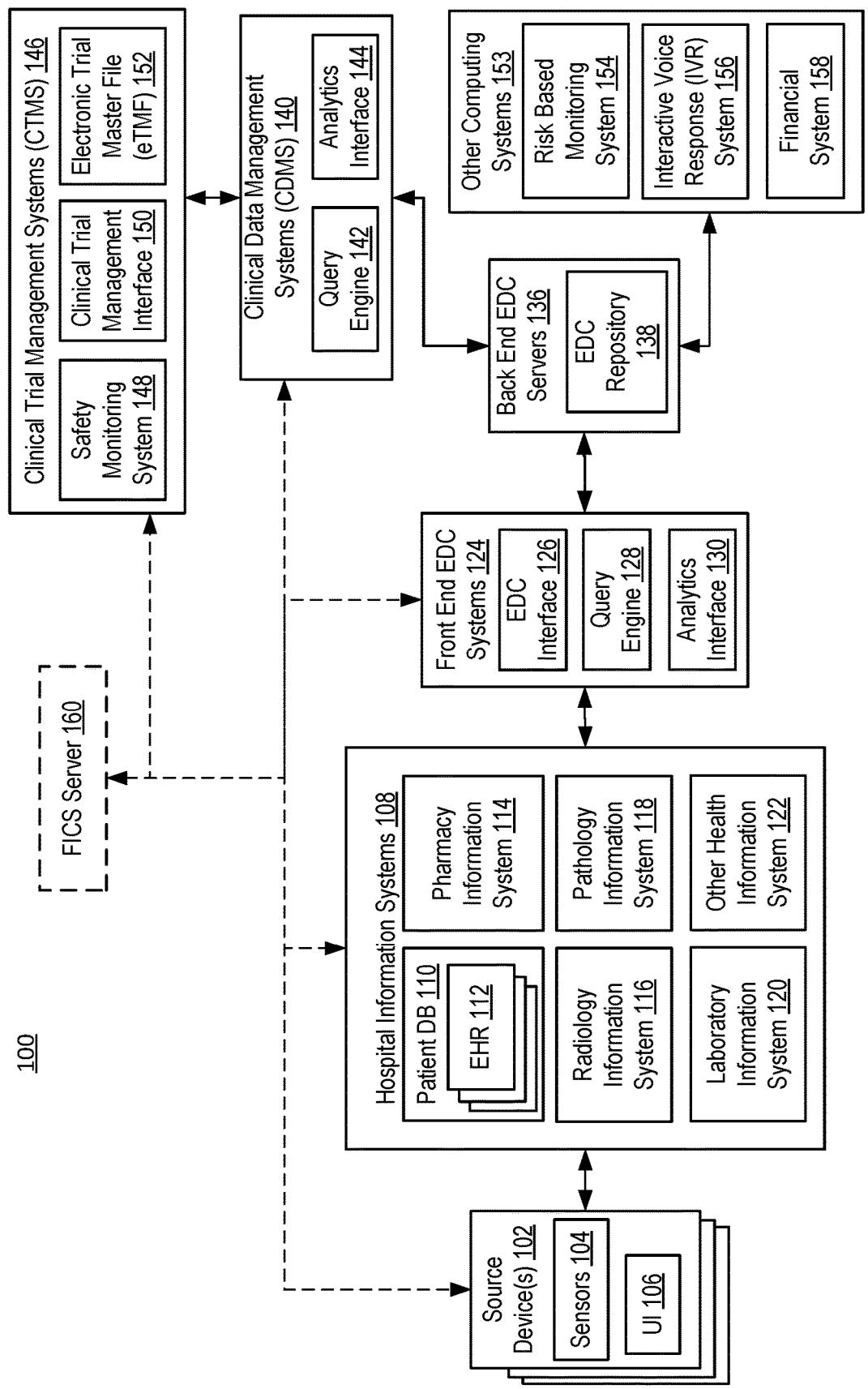
FIG. 1 illustrates a block diagram of an example computer network environment comprising fragmented systems for the capture and use of medical data and the addition of an interoperable platform for reducing redundancy in medical database management.

Patient-specific medical data obtained in hospitals, pharmacies, testing facilities, and/or homes, e.g., via medical devices, are often relied on by a variety of different electronic database systems and servers and for a variety of end goals. Unfortunately, such patient-specific data capture can lack coordination or standardization, and often occurs in fragmented silos. Thus, conventional methods and systems for patient-specific data capture often lead to inconsistencies in the input of data. Furthermore, patient-specific data captured at disparate settings are often managed by different platforms and vendors. Each platform or vendor may use different standards for entering medical data based on their respective end goals. For example, such standards (e.g., the format or syntax for entering medical data, required data fields, level of privacy or encryption, etc.) can often differ for patient-specific data captured for clinical trial research, billing and reimbursement, or medical record keeping. Thus, the same patient-specific data may need to be reentered, reformatted, and/or refined at different electronic data capture systems for different end goals. Such fragmentation in medical data capture often contributes to inefficiencies in producing clinical data, suboptimal quality in the clinical data, and rising costs in research, development, and healthcare delivery.

The discordance of medical data capture sites and databases can be a major burden for healthcare and research. For example, erroneous patient data entry into electronic systems can compromise patient safety and may be implicated in medical liability claims. The fragmented and repetitive nature of conventional patient-specific medical data capture can often lead medical personnel to endure more screen time and less face time, which can be a major source of healthcare worker stress and burnout. Furthermore, medical data capture sites often do not sufficiently raise the awareness of, or provide the public access to, ongoing clinical studies, which often leads to a significant portion of medical data capture sites failing to enroll a single patient. For example, the vast majority of eligible global cancer patients are often left out of participation in clinical trials to develop essential cancer medicines. Even further, poor quality medical data and manual, redundant processes for capturing medical data, both of which can be mitigated by optimizing technology, often contribute to rising healthcare and research costs. As will be discussed herein, various embodiments for systems and methods are described for reducing redundancy in medical database management.

Patient-specific data may be presented in many forms. For example, patient-specific data may include, but is not limited to, patient-specific raw data (e.g., unstructured and/or uncoded data received from source devices at a point-of-care of a patient), the patient-specific electronic health record (EHR), and patient-specific electronic data capture (EDC) data (e.g., presented to clinical trial sites). As used herein, a form may refer to the structure, format, and types of data fields for a desired or required presentation of patient-specific data by a specific computing system (e.g., a hospital information system, a clinical trial management system, a financial and billing computing system etc.). Form may also include the desired or required language or vocabulary to be used for the entry of data in those data fields. Systems and methods presented herein discuss converting or translating patient-specific data from an earlier form (e.g., patient-specific raw data) to a new form required by the destination system. As used herein, a translation or a conversion may include a transformation of the presentation of patient-specific data from a previous form to a new form, including the transfer of patient-specific data from the structures, formats, and types of data fields of the previous form to the structures, formats, and types of data fields of the new form, and any changes in language or vocabulary of terms used in the patient-specific data.

Computing Systems Used in the Network Environment for Medical Database Management FIG. 1 illustrates a block diagram of an example computer network environment 100 comprising fragmented systems for the capture and use of medical data and the addition of an interoperable platform for reducing redundancy in medical database management. The fragmented systems may include one or more source devices 102, one or more hospital information systems 108, one or more front end electronic data capture (EDC) systems 124, one or more back end electronic data capture (EDC) servers 136, one or more clinical data management systems 140, one or more clinical trial management systems (CTMS) 146, a risk based monitoring system 154, an interactive voice response system 156, and a financial system 158. Each of the systems of network environment 100 may communicate with one or more of the remaining systems via a communication network. FIG. 1 further illustrates a server for an interoperable platform (e.g., the front end interoperable capture system (FICS) server 160) for reducing redundancy in medical database management. The FICS server 160 may be added (e.g., addition shown as dotted lines) to a network comprising the fragmented systems for the capture and use of medical data, in order to reduce redundancy in medical database management. As will be further discussed in relation to FIG. 2, the FICS server 160 may help eliminate redundancies in medical database management, by more efficiently managing the flow of patient-specific data through the above described fragmented systems. Furthermore, FIG. 2 will describe the components of the FICS server 160 and how the addition of the FICS server 160 to the network environment of the fragmented systems alters the relationship of the fragmented systems in greater detail.

The source devices 102 may comprise standalone or portable computing device (e.g., a mobile device, personal digital assistant, laptop, tablet computers, smart camera, etc.) having one or more of the subcomponents described herein for allowing a user (e.g., a medical personnel, a patient, a caretaker, etc.) to obtain measurements for and/or input patient-specific medical data. Each source device 102 may include a user interface 106 for allowing the user to enter patient-specific data, e.g., as patient-specific raw data. In some aspects (e.g., where the source device is a wearable, medical device, and/or a medical instrument), the source device may include one or more sensors 104 for obtaining measurements comprising patient-specific raw data. For example, the sensors 104 may comprise a thermometer for obtaining the temperature of the patient, sphygmomanometer for obtaining a blood pressure of the patient, a blood glucose meter for obtaining blood glucose levels of a patient, and the like.

The hospital information systems 108 may include one or more computing systems that facilitate the import of patient-specific data and the storage of patient-specific electronic health records (EHR) 112 in a database (e.g., patient database 110). Hospital information systems 108 may include, but are not limited to, a pharmacy information system 114, a radiology information system 116, a pathology information system 118, a laboratory information system 120, and other health information systems 122.

The front end EDC systems 124 comprise one or more computing systems that allow users (e.g., medical personnel, researchers, scientist, etc.) to enter, access, and/or analyze electronic patient-specific data used, for example, in clinical trials, clinical data management, risk based monitoring, or finances and billing. The front end EDC systems 124 may include a user facing interface (e.g., EDC interface 126) that can receive electronic patient-specific data to be entered to be stored in the back end EDC servers 136. The EDC interface 126 may include, for example, a user interface, an input output module, a display, and other functionalities that allow the entry of data. The front end EDC systems 124 may include a query engine 128 that may comprise a software, program, module, and/or plug-in allowing a user to search for specific patient-specific EDC data, and receive query results (e.g., answers to questions, search results, location of a specific EDC data or file, etc.). An analytics interface 130 may allow a user to analyze results, trends, predictions, and/or comparisons of patient-specific EDC data stored in the back end EDC servers 136, e.g., in an audio, visual, and/or textual form.

The back end EDC servers 136 may comprise one or more servers for storing patient-specific EDC data in one or more databases, such as EDC repository 138. For example, the EDC repository 138 may be updated by and/or accessed by the front end EDC systems 124. In some aspects, other computing systems of network environment 100 (e.g., CDMS 140, CTMS 146, risk based monitoring system 154, IVR System 156, and financial system 158) may access, update, and/or retrieve, and/or copy EDC data stored in the back end servers 136. These other computing systems may include separate databases that also store a subset of the EDC data stored in the back end EDC servers 136. In some aspects, the back end EDC servers 136 may be remotely located from the front end EDC systems 124. With its association with the front end EDC systems 124, the back end EDC servers 136 may comprise an electronic data management system.

The CDMS 140 may comprise electronic data management system for storing and accessing clinical trial data in compliance with applicable regulatory requirements. For example, the CDMS 140 may comprise one or more servers that access the back end EDC servers 136 to query and/or analyze clinical trial data from the databases of patient-specific EDC data (e.g., EDC repository 138). In some aspects, the CDMS 140 may include a query engine 142 and an analytics interface 144. The query engine 142 may comprise a software, program, module, and/or plug-in allowing a user to search for clinical data from stored patient-specific EDC data, and receive query results (e.g., answers to questions, search results, location of a specific clinical data or file, etc.). An analytics interface 144 may allow a user to analyze results, trends, predictions, and/or comparisons of clinical data generated from the patient-specific EDC data stored in the back end EDC servers 136, e.g., in an audio, visual, and/or textual form. In some aspects, the clinical data management systems 140 may reformat, aggregate, and/or otherwise transform patient-specific EDC data into clinical trial data.

The CTMS 146 may comprise an electronic data management system whereby sponsors of a clinical trial can enter data, upload documents, analyze data, track documents, and monitor the progress of clinical trials. The CTMS 146 may comprise one or more servers that communicates with the back end EDC servers 136 to request and receive patient-specific EDC data relevant for clinical trials. The CTMS 146 may comprise a safety monitoring system 148, a clinical trial management interface 150, and an electronic trial master field (eTMF) 152. The safety monitoring system 148 may comprise any software, application, program, or module to assist with monitoring safety in clinical trials in accordance with regulatory requirements. The clinical trial management interface 150 may comprise a user interface, application interface, software, application, or program for allowing a user to initiate, conduct, and/or manage a clinical trial. The eTMF 152 may comprise an electronic repository for storing and sharing essential clinical trial documents, images and other digital content in compliance with applicable regulatory requirements.

The network environment 100 may also include other computing systems 153 that may rely on stored patient-specific EDC data, such as the risk based monitoring system 154, the IVR system 156, and the financial system 158. Such patient-specific EDC data may need to be reconverted, reformatted, augmented, and/or manually reentered based on the requirements of the given computing system or function of the given computing system (e.g., risk monitoring, IVR, billing, etc.).

Figure 2:
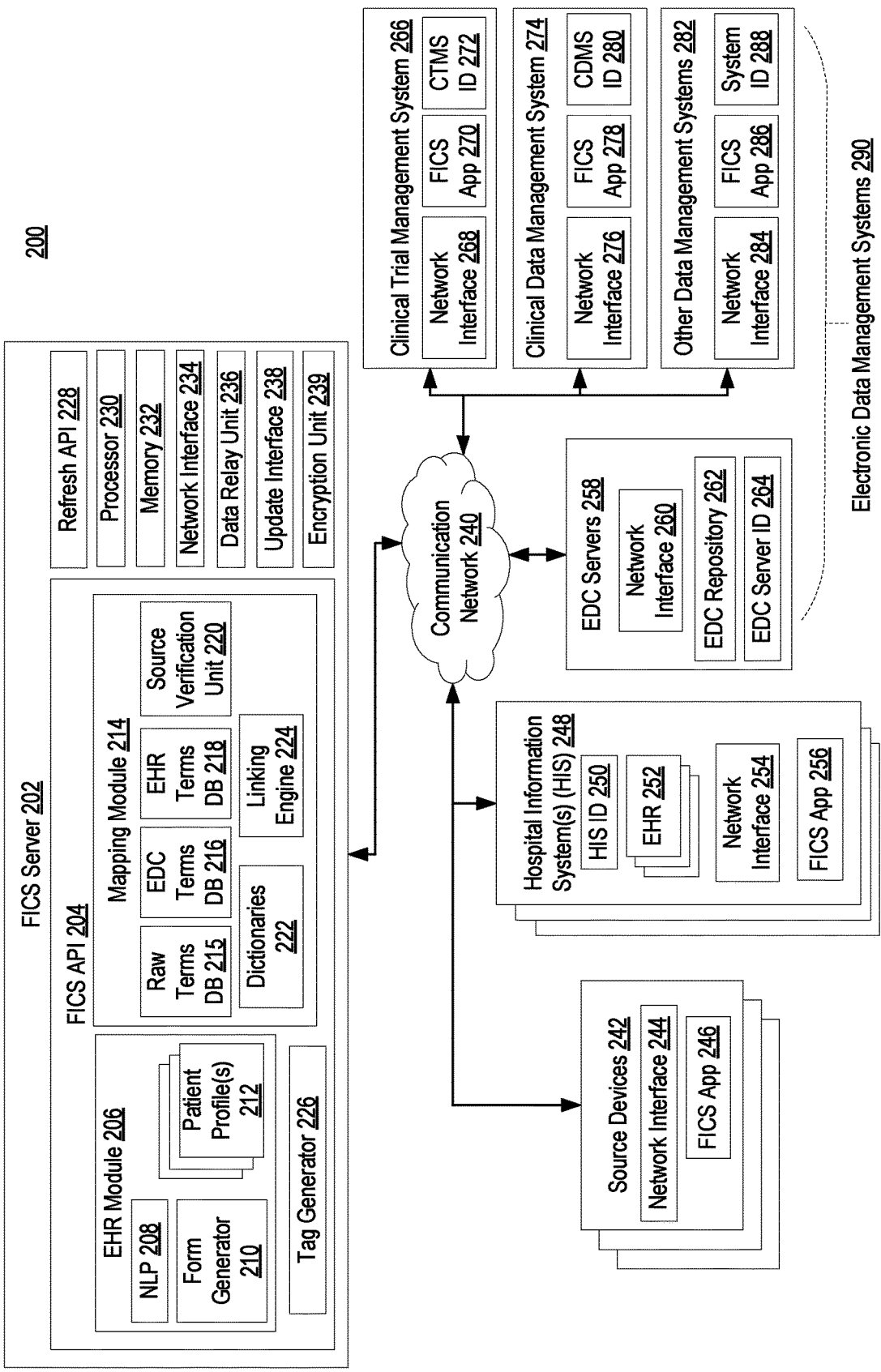
FIG. 2 illustrates a block diagram of an example computer network environment for reducing redundancy in medical database management using an interoperable platform, according to an example embodiment of the present disclosure.

System Components for the Interoperable Platform for Reducing Redundancy in Medical Database Management FIG. 2 illustrates a block diagram of an example computer network environment 200 for reducing redundancy in medical database management using an interoperable platform, according to an example embodiment of the present disclosure. Furthermore, computer network environment 200 may result from a transformation, via the interoperable platform, of a previously fragmented environment for the capture and use of medical data by disparate and/or fragmented systems. The transformation may help reduce redundancy and fragmentation in medical database management by allowing the capture and storage of patient-specific data to be more standardized (e.g., by automatically reformatting data to other formats), more synchronized across medical databases (e.g., by periodically ensuring that one or more databases are updated with the latest patient-specific data), and more readily accessible by users (e.g., by automatically directing patient-specific data to destination systems and seamless allowing data to be retrieved, tagged, and/or otherwise compiled based on clinical trials). Furthermore, the transformation may improve the collective processing time of various operations (e.g., requesting, searching for, and compiling relevant clinical information for a clinical trial) with the use of tags generated in real-time right after the capture of patient-specific raw data from disparately located devices, and then directing the patient-specific data with relevant tags to appropriate locations. Such an approach is proactive as compared to conventional methods of that rely on the initiation of a clinical trial to communicate with clinics and hospitals to inquire for relevant patient-specific data. Furthermore, the standardization of patient-specific data and dynamic generation of patient-specific forms (e.g., by prompting the operator to provide additional data based on a previous input and/or based on an insufficient response) allows for greater accuracy and reliability of patient-specific data exchanged across the disparate computing systems.

The network environment 200 may comprise a server for an interoperable platform for reducing redundancy in medical database management (e.g., front end interoperable capture system (FICS) server 202), a plurality of source devices 242, one or more hospital information systems 248, and a plurality of electronic data management systems 290. The plurality of electronic data management systems 290 may include, but are not limited to, one or more of electronic data capture (EDC) servers 258, a clinical trial management system 266, a clinical data management system 274, and other data management systems 282 (e.g., risk based monitoring systems, financial and/or billing systems, health insurance claim systems, etc.). Each of the systems of network environment 100 may communicate with one or more of the remaining systems via a communication network 240. The communication network 240 may comprise wired and wireless networks. Examples of the wired networks may include a wide area network (WAN) or a local area network (LAN), a client-server network, a peer-to-peer network, and so forth. Examples of the wireless networks comprise Wi-Fi, a global system for mobile communications (GSM) network, and a general packet radio service (GPRS) network, an enhanced data GSM environment (EDGE) network, 802.5 communication networks, code division multiple access (CDMA) networks, Bluetooth networks or long term evolution (LTE) network, LTE-advanced (LTE-A) network or 5th generation (5G) network.

Furthermore, each source device 242, hospital information system 248, EDC server 258, clinical trial management system 266, and clinical data management system 274 may share one or more components and perform one or more functions previously described for source device 102, hospital information system 108, back end EDC server 136, clinical trial management system 146, and clinical data management system 140 respectively. For example, one or more hospital information systems (HIS) 248, like the hospital information systems 108 shown in FIG. 1, may store patient-specific electronic health records (EHR) 252, like EHR 112. As another example, each EDC server 258 may include an EDC repository 262 that, like EDC repository 138 shown in FIG. 1, stores patient-specific EDC data. In at least one embodiment, the FICS server 160 may reduce or eliminate the need for a distinct front end electronic data capture system (e.g., as in front end EDC system 124 shown in FIG. 1) by automating converting patient-specific data obtained from source devices 242 and hospital information systems 248 into patient-specific EDC data. In some aspects, components or functionalities previously described for the front end EDC systems 124 may be subsumed by or performed by one or more devices or systems associated with the hospital information systems 248. Also or alternatively, components or functionalities previously described for the front end EDC systems 124 may be subsumed by or performed by one or more devices or systems associated with the EDC servers 258.

In some aspects, each system of the network environment 200 (e.g., the FICS server 202, each source device 242, each hospital information system 248, or each electronic data management system 290) may include a network interface (e.g., network interface 234, network interface 244, network interface 254, network interface 260, network interface 268, network interface 276, and network interface 284) allowing the respective system to communicate with other systems over the communication network 240. For example, the respective network interface may comprise a wired interface (e.g., electrical, RF (via coax), optical interface (via fiber)), a wireless interface, a, modem, etc.

The FICS server 202 may include a local or a remote computing system that functions as an interoperable platform for reducing redundancy in medical database management. The FICS server 202 may comprise a FICS application programming interface (API) 204 for providing and managing an interface for applications (e.g., FICS App 246, FICS App 256, FICS App 261, FICS App 270, FICS App 278, and FICS App 286, etc.) used by one or more systems of network environment 200 to reduce redundancy in medical database management. The ability of users at each computing system to use the applications to contribute to and/or avail the opportunity of having reduced redundancy in medical database management will be explained further herein. The respective applications (FICS applications) may comprise cloud-native web-based applied applications built on React/Javascript. Furthermore the FICS applications may include user interfaces that allow data entry based on forms (e.g., with structured fields). Also or alternatively, the FICS App may allow entry of natural, unstructured patient-specific data (e.g., patient-specific raw data) that may be arranged into structured fields by the FICS server 202. Furthermore, the FICS applications may allow the user to visualize data stored in medical databases (e.g., tables, aggregate information, dashboard, etc.). Each system leveraging the application may be identifiable by the FICS server 202 via a respective device and/or system ID (e.g., source device ID 243, hospital information system (HIS) ID 250, EDC server ID 264, CTMS ID 272, CDMS ID 280, system ID 288), allowing the FICS server to efficiently and accurately receive requests for, retrieve, process, convert, and relay information (e.g., patient-specific data) between systems. For example, the FICS server 202 may receive patient-specific data from a given source device 242, identify the source device 242 by its source device ID 243, convert the patient-specific data into a form appropriate for an electronic health record 252, identify a HIS that is a destination for the EHR 252 by mapping the source device ID 243 to a HIS ID 250 associated with the HIS 248, and send the EHR to the identified HIS 248.

The FICS server 202 may include an EHR module 206, a software and/or hardware subcomponent of the FICS server 202 used for generating patient-specific EHR data. For example, the EHR module may generate patient-specific EHR data by prompting the input of EHR data via a source device 242 and/or by converting patient-specific health data already received from the source device 242 into patient-specific EHR data (e.g., by reformatting or changing a syntax of the patient-specific health data). The EHR module 206 may comprise a natural language processor (NLP) 208, a form generator 210, and a plurality of patient profile(s) 212 associated with a plurality of patients. The NLP 208 may comprise one or more processors, processing units, programs, applications, and/or plug-ins for processing and analyzing natural language data (e.g., audio and/or textual natural language). The NLP may include for example, a parser, a lexer, and tokenizer to determine, e.g., from a string of inputted natural language, recognizable tokens for processing by the FICS server 202. The form generator 210 may comprise a program, application, and/or plug-in for generating data fields for an electronic health record form. The specific identity of, type of, quantity of, and extent of the data fields of the EHR may vary based on the patient. In some aspects, the data fields may vary based on the hospital information system or electronic data management system seeking the EHR. In further aspects, one or more subsequent data fields of an EHR form may be dynamically generated, based on a completion (e.g., entry of a response) for another data field of the EHR form. As data fields of an EHR form are populated by responses pertaining to a patient, the populated EHR form having information specific to the patient may be referred to as patient-specific EHR for simplicity. Each patient-specific EHR may be linked to, or otherwise associated with, a patient profile. The patient profiles 212 may comprise a repository of identifications of different patients to map, associate, link, and/or reference various patient-specific data (e.g., patient-specific EHR data) for each patient.

The FICS server 202 may also include (e.g., as part of its FICS API 204) mapping module 214. The mapping module 214 may comprise a software and/or hardware subcomponent of the FICS server 202 used for mapping and converting patient-specific medical data of a first type to patient-specific medical data of a second type. The types of patient-specific data may include, but is not limited to, patient-specific raw data, the patient-specific electronic health record (EHR), and patient-specific electronic data capture (EDC) data. Patient-specific raw data includes data obtained at source devices 102. The patient-specific raw data may include, for example, uncoded data pertaining to a health or medical history of a patient. The raw data may be obtained from medical devices (e.g., instrument measurements), handwritten notes scanned and uploaded on to the source device, data inputted via forms generated the FICS server 202, etc. Patient-specific EHR may comprise coded and systematized collection of health information of a patient in a digital format. Patient-specific EHR may include a range of data, including, but not limited to, demographics, medical history, medication and allergies, immunization status, laboratory test results, radiology images, vital signs, personal statistics like age and weight, and billing information. While EDC data may include medical data pertaining to a specific clinical trial, patient-specific EDC data may include EDC data attributed to a specific patient. EDC data and/or patient-specific EDC data may be further divided and/or customized (e.g., based on preferred syntax, form, etc.) based on the electronic data management system 290 that utilizes it (e.g., clinical trial management system 266, clinical data management system 274, or other data management systems 282). For each of the above described types of patient-specific data, the mapping module 214 may store repository or database of terms associated with each type (e.g., raw terms 215, EDC terms 216, EHR terms 218).

The mapping module 214 may also include one or more dictionaries (e.g., dictionaries 222) to determine the definition of each term. For example, the dictionaries may be a program that identifies the scope of a given term based on other terms that fall within the given term. The mapping module 214 may include a linking engine 224, which may comprise a program, application, software, or code that may periodically form linkages or associations between one term (e.g., for a first type of patient-specific data) with another term (e.g., for a second type of patient-specific data). For example, the linking engine 224 may be used to form an association between a common name for a symptom that may be a term used in patient-specific raw data, and a clinical name for the symptom, as may be used in patient-specific EDC data. In some aspects, the FICS server 202 may identify information it receives as belonging to one or more of the above-described types of patient-specific data based on the source system sending the information. Thus, the FICS API 204 can facilitate mapping of terminology used between different forms of presentation of patient-specific data (e.g., patient-specific raw data versus patient-specific EHR versus patient-specific EDC forms). Patient-specific data entered under conformance of a specific data dictionary can be translated to the appropriate matching term of another data dictionary. For example, a medical personnel may enter, at the source device 242, medication for a patient, in accordance to the RX NORM standard. The FICS API 204 can translate this patient-specific data to the WHO DRUG standard typically used for datasets in regulatory submission.

The source verification unit 220 may be a subcomponent of the mapping module 214 with instructions to identify the source system for the information (e.g., a source device 242, a hospital information system 248, an EDC server 258, a clinical trial management system 266, a clinical data management system 274, or other data management system 282). In some aspects, the source verification unit 220 and/or the linking engine 224 may be used to map or associate one or more source systems to one another, e.g., for the purpose of relaying information to the right destination. For example, one or more source devices 242 may be associated with a specific hospital information system 248 (e.g., such as various computing systems of a pharmacy). Furthermore, the source verification unit 220 may track or identify various source systems by their respective system or device identification (e.g., source device ID 243, hospital information system (HIS) ID 250, EDC server ID 264, CTMS ID 272, CDMS ID 280, system ID 288).

The FICS server 202 may include a tag generator 226. The tag generator 226 may be a software and/or hardware component of the FICS server 202 that may generate metadata or tags based on received patient-specific data. The tags may be based on processing and identifying various characteristics of a received patient-specific data, for example, the patient associated with the patient-specific data, the source system from which the patient-specific data originates, the nature of the patient-specific data (e.g., diagnosis, treatment, drugs, therapy, billing, check-up, measurement or reading, etc.), the time and/or date of generation or receipt of the patient-specific data, an intended recipient, any clinical trial associated with the patient-specific data, any drug development associated with the patient-specific data, etc.

The FICS server 202 may include a refresh application program interface (API) 228, a processor 230, memory 232, a network interface 234, a data relay unit 236, an update interface 238, and an encryption unit 239. The refresh API 228 may comprise any application, program, software, code, or plug-in that allows operations and data transfers performed since the last refresh accessible at the next refresh, at periodic intervals, thus allowing the transfer, reformatting, conversion, and storage of medical data to occur in real or near real time. The processor 230 may comprise any one or more types of digital circuit configured to perform operations on a data stream, including functions described in the present disclosure. The memory 232 may comprise any type of long term, short term, volatile, nonvolatile, or other memory and is not to be limited to any particular type of memory or number of memories, or type of media upon which memory is stored. The memory may store instructions that, when executed by the processor 230, can cause the FICS server 202 to perform one or more methods discussed herein. The data relay unit 236 may comprise any application, program, software, code, or plug-in that may receive patient-specific data, identify (e.g., via tags or metadata associated with the patient-specific data) an intended destination, determine a network address associated with the intended destination, and sending the patient-specific data. In some aspects, the patient-specific data may be preconverted to the desired format, syntax, and/or structure of the intended destination. In other aspects, the data relay unit 236 may, after identifying the intended destination, cause the mapping module 214 to convert and/or transform the patient-specific data to the desired format, syntax, and/or structure (e.g., patient-specific raw data to patient-specific EHR, patient-specific raw data to patient-specific EDC data, patient-specific EHR to patient-specific EDC data, etc.). The update interface 238 may comprise any application, program, software, code, or plug-in used to allow an operator or an external system to update one or more databases or repositories of FICS server 202. For example, the update interface 238 may allow an operator to enter, into dictionaries 222, raw terms database 215, EDC terms database 216, and/or EHR terms database 218, e.g., for a newly identified disease or symptom, or a newly discovered treatment. As is to be appreciated patient-specific data may include sensitive or confidential information. Intended destinations may not necessarily be authorized to view all or certain aspects of patient-specific data. Based on the intended destination of a patient-specific data, the encryption unit 239 may comprise an application, program, software, code, or plug-in to implement a method to encrypt and decrypt electronic protected health information. The encryption and decryption protocols implemented by the encryption unit 239 may be pursuant to regulations (e.g., HIPAA). In some aspects, the FICS server 202 can create appropriate restrictions to medical database access. For example, patient-specific data in various forms generated by the FICS (e.g., from patient-specific raw data submissions) can remove, encrypt, and/or limit access to protected health information.

Conventional Methods of Managing Medical Databases

Figure 3:
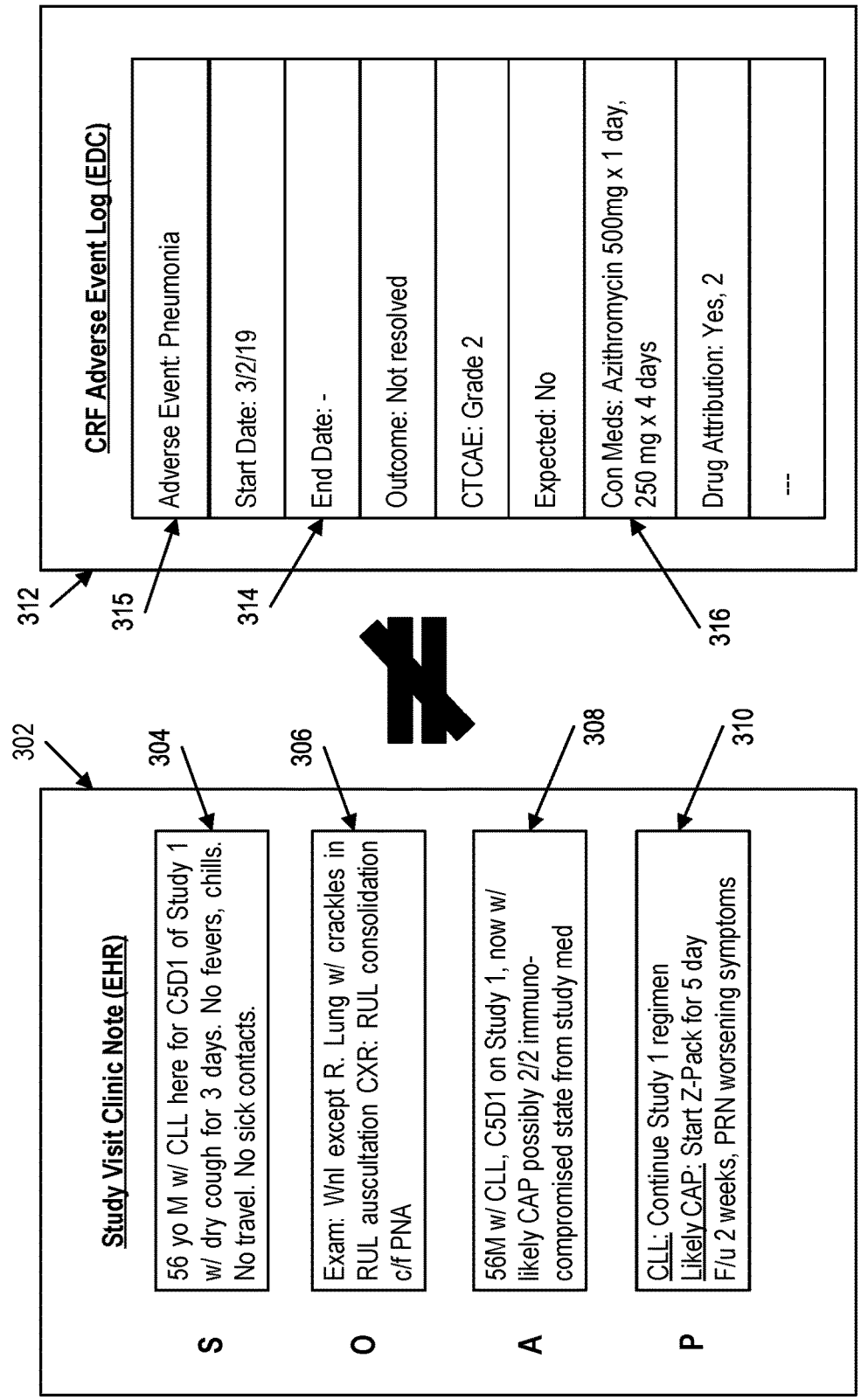
FIG. 3 illustrates an example of fragmented data capture interfaces showing inconsistencies in the captured patient-specific data.

FIG. 3 illustrates an example of fragmented data capture interfaces showing inconsistencies in the captured patient-specific data. The patient-specific data entered in both data capture interfaces pertain to the same patient and for the same medical experience (e.g., medical diagnosis, symptom, treatment, etc.), and yet the differences in format, syntax, and/or structure of each data capture interfaces reveal inconsistencies. For example, data capture interface 302 shows an example patient-specific electronic health record (EHR) entered as a clinical note during a study visit. The patient-specific EHR is entered in the form of a subjective, objective, assessment, and plan (SOAP) format typically used in electronic health records. The subjective section 304 may prompt an input of the chief complaint of the patient, including the symptoms and history of the present illness. The objective section 306 may prompt an input of any information that a healthcare provider may observe or measure from the patient's current presentation (e.g., vital signs, lab results, physical examination results, etc.). The assessment section 308 may prompt input of information of the patient's progress towards recovery, written from the physician's perspective. The plan section 310 may prompt input of the plan that a health care provider has for the treatment of the patient's illness. However, as shown by the entry of these sections, the entry of information into a conventional EHR forms often includes unstructured free text inundated with medical lingo and abbreviations (e.g., CLL, C5D1, Wnl, RUL, CXR, F/u, c/f, etc.). Furthermore, the format of data structures prompting the entry of information (e.g., SOAP) can often result in missing information that may be key data elements for other medical contexts and databases (e.g., clinical trials).

For example, data capture interface 312 shows an example patient-specific EDC data entered as part of a case report form (CRF) adverse event log for the same patient having the same medical experience. The CRF adverse event log shows that the patient suffered an adverse event (e.g., pneumonia), and may be used to track the effectiveness of a treatment in a clinical trial. However, the data capture interface 312 shows that there are key trial data elements that are missing. For example, the data capture interface 312 is missing the end date 314, an indication of additional adverse events 315 (e.g., such as CLL mentioned in the patient-specific EHR) and other medications 316. Such elements may typically be required for input into a case report form during the generation of patient-specific EDC data. However, systems and methods presented herein may allow such key data elements to be prompted for input or otherwise obtained from an earlier stage of patient-specific data capture (e.g., at the capture of patient-specific raw data). The original source of patient-specific data (e.g., patient-specific raw data), and the systems and methods of prompting input of that patient-specific data may automatically be used to populate forms and data structures required by different medical databases (e.g., EHR, EDC data). As will be discussed herein, the automatic generation of forms from patient-specific raw data may eliminate or reduce inconsistencies of information in different forms and missing data elements.

Reducing Redundancy in Medical Data Capture

Figure 4:
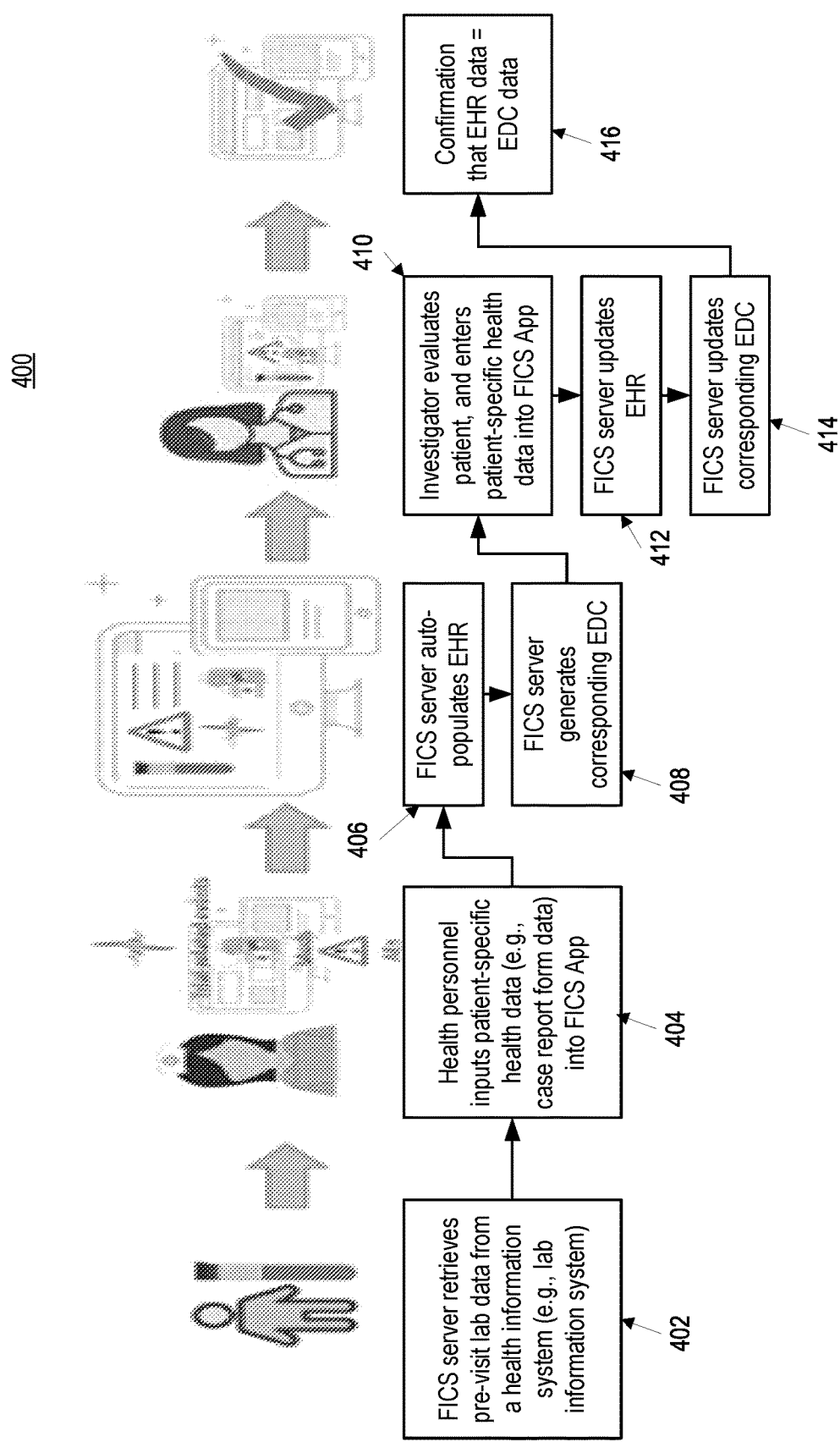
FIG. 4 illustrates a flow chart showing how the interoperable platform reduces redundancy in medical data capture, according to an example embodiment of the present disclosure.

FIG. 4 illustrates a flow chart showing how the interoperable platform reduces redundancy in medical data capture, according to an example embodiment of the present disclosure. Specifically, FIG. 4 illustrates how the FICS server (e.g., FICS server 160 as shown in FIG. 1 or FICS server 202 shown in FIG. 2) helps to reduce redundancy in the way patient-specific data is transferred, converted, reformatted, and updated across medical database, which helps to eliminate or reduce issues of inconsistent and missing patient-specific data previously shown in FIG. 3. Method 400, shown in FIG. 4, may be performed by a processor of the FICS server (e.g., processor 230 of FICS Server 202), based on information received via applications (e.g., FICS App 246, FICS App 256, FICS App 270, FICS App 278, FICS App 286) running on various computing systems. For demonstration purposes, FIG. 4 illustrates a scenario where a patient undergoes lab testing (e.g., blood testing) and then comes to see a health personnel (e.g., a family physician) for a physical check-up. The lab testing may be performed in a lab facility associated, where lab results may be uploaded on to a lab information system (e.g., an example of a health information system 248). The physical check-up may occur at a hospital or clinic where the health personnel may enter patient-specific data via a source device 242 (e.g., an office computer next to the bedside of the patient). Furthermore, the patient may have ongoing conditions and/or ongoing treatment that may also be relevant for clinical researchers. Such clinical researchers may be involved on a clinical trial and may be able to access and/or update patient-specific data via a clinical trial management system 266. Method 400 shown in FIG. 4 may reduce redundancy in steps conventionally performed by the hospital information systems, health personnel, and clinical researcher in accessing, entering, and updating patient-specific data.

For example, before the patient's arrival at the health personnel's office, the health personnel (e.g., patient's family physician) may want to know the patient's lab test results (e.g., blood test results) The health personnel may request the lab test results via FICS app 246 on source device 242 (e.g., the health personnel's office computer). Responsive to this request, the FICS server may retrieve pre-visit lab data from a health information system (e.g., lab information system of the lab testing facility) (block 402). This step may be an improvement from conventional methods whereby the patient or the lab technician may be tasked with manually delivering the patient's lab results, and the health personnel spending time and effort to understand the lab test results, and enter the lab test results into the source device 242.

The health personnel may then analyze the pre-visit lab data (e.g., by accessing it through their FICS app 246 on their source device 242), in preparation for the patient visit. After seeing the patient during the visit, the health personnel may enter in patient-specific data based on the patient visit into their FICS app (block 404). The lab test results and patient-specific data entered by the physician may be considered as patient-specific raw data because such data may not yet be coded or arranged in a required form or syntax by various medical databases. The FICS server 202 may receive the patient-specific data entered by the health personnel and lab testing data and may automatically auto-populate an electronic health record (EHR) associated with the patient (block 406). The FICS server 202 may also use the received patient-specific raw data to generate fields for corresponding patient-specific EDC data (block 408). For example, as previously discussed, the FICS server 202 may rely on dictionaries of terms used in raw data, EHR data, and EDC data to map inputted terms in the patient-specific raw data to the corresponding terms required by the EHR and EDC forms. In some aspects, the FICS server may determine whether a specific form (e.g., EHR or EDC form) requires additional entries (e.g., end data of an illness) and may prompt a user of the FICS app (e.g., health personnel) for additional input.

The patient-specific EDC data may be used for clinical researchers. For example, a research investigator may be particularly interested in an illness that the patient has had or is having. After analyzing EDC data associated with the patient (e.g., via FICS app 278 on clinical data management system 274), the investigator may want to consult the patient to learn more about the illness and any ongoing treatment. The investigator may evaluate the patient and enter additional patient-specific raw data (e.g., notes about their observations about the patient's recovery) into their FICS app (block 410). After receiving the patient-specific raw data, the FICS server 202 may automatically update the patient-specific EHR based (block 412), and may automatically update corresponding patient-specific EDC data (block 414).

Furthermore, as previously discussed in relation to refresh API 228, the FICS server 202 may routinely synchronize and update medical databases managed by the FICS server 202 in real or near real-time. This may occur as a result of ensuring completion of operations (e.g., data transfers, data conversions, data consistency checks between databases, etc.) initiated since the previous refresh interval before each subsequent refresh interval. In some aspects, completion of operations may entail prompting users of the FICS API that previously entered patient-specific data to enter any required information to populate relevant forms (e.g., EHR, EDC forms used CTMS and CDMS, etc.). By performing such synchronization and routine update processes, the FICS server may check and confirm that patient-specific data entered in different forms (e.g., EHR and EDC) are consistent (block 416).

Figure 5:
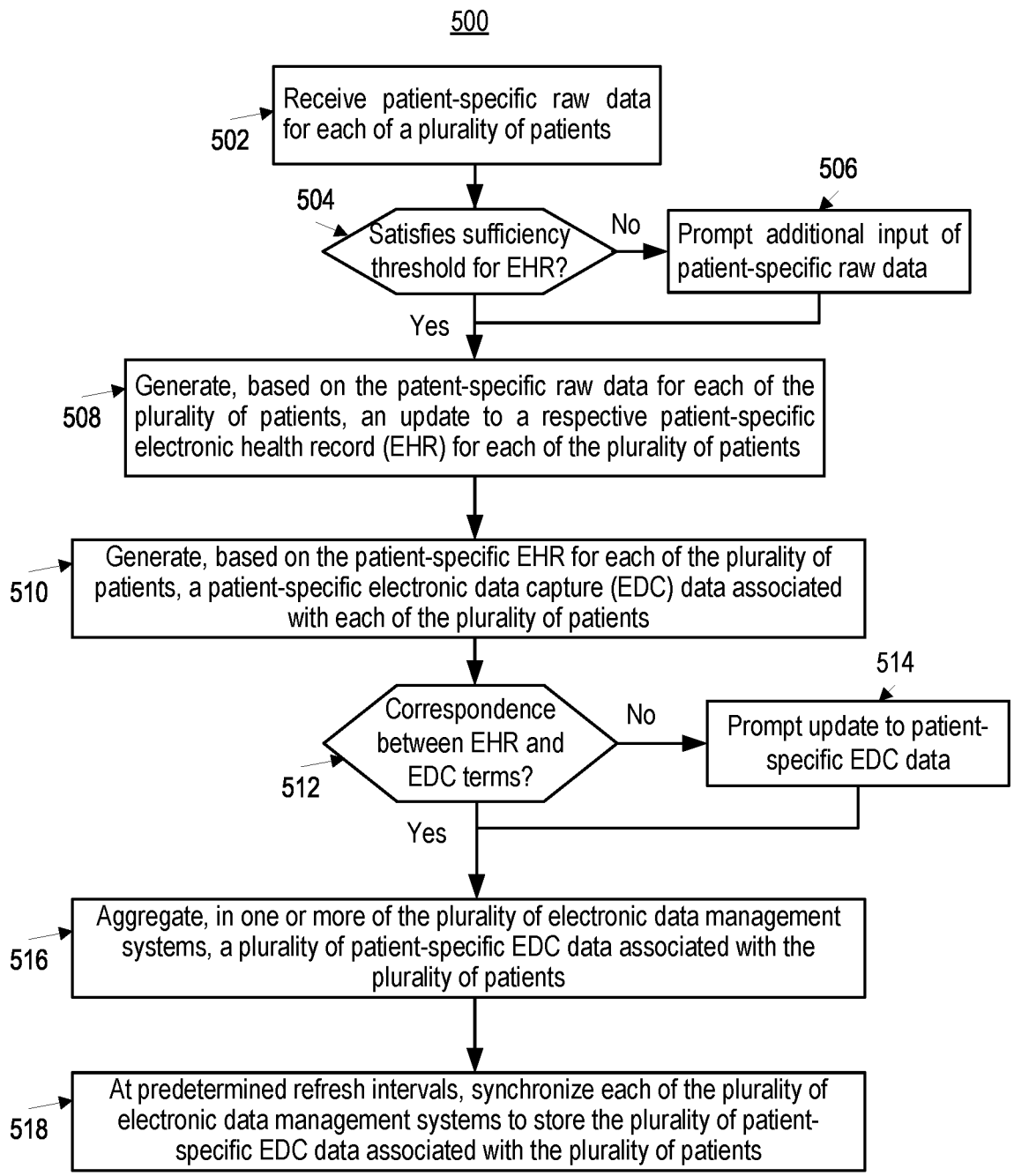
FIG. 5 illustrates a flow diagram of an example method of reducing redundancy in medical database management, according to an example embodiment of the present disclosure.

Automated Data Capture, Translation, and Synthesis of Patient-Specific Data Across Platforms for Medical Database Management FIG. 5 illustrates a flow diagram of an example method 500 of reducing redundancy in medical database management, according to an example embodiment of the present disclosure. One or more steps of method 500 may be performed by processor 230 of FICS server 202, e.g., based on instructions stored in memory 232, and based on information received via applications (FICS apps) running on various other devices and computing systems.

Method 500 may begin by receiving patient-specific raw data for each of a plurality of patients (block 502). As previously noted, patient-specific raw data may include, for example, uncoded data pertaining to a health or medical history of a patient. The raw data may be obtained from medical devices (e.g., instrument measurements), handwritten notes scanned and uploaded on to the source device, data inputted via forms generated the FICS server 202, etc. In some aspects, for example, where the patient-specific raw data is handwritten or is in natural language or unstructured form, the NLP 208 of the FICS server 202 may recognize lexical tokens and attempt to organize the patient-specific raw data into categories that are useful in the generation of entries for specific forms (e.g., EHR).

For each patient, the FICS server may determine whether the received patient-specific raw data satisfies a sufficiency threshold for an electronic health record (EHR) (block 504). If the sufficiency threshold is not satisfied, the FICS server may prompt additional input of patient-specific data (block 506). For example, the FICS server 202 may rely on the form generator 210 to create a template EHR. The EHR may be auto populated with the patient-specific raw data. However, if data fields of the template EHR lack, or are determined as being insufficient in response (e.g., by way of the EHR module 206 learning whether lexical tokens satisfy information requested within a data field), the FICS server may determine that the sufficiency threshold is not met. In some aspects, the process of verifying completion may occur at the local level. For example, the user interface of the FICS application can verify whether all or most of the required data fields in a specific form are complete. If any or a sufficient number of the required data fields are incomplete (e.g., a missing date of birth for patient demographics), the user interface of the FICS application can alert the user (e.g., a medical personnel) that the form is incomplete, and may not permit the user from sending the patient-specific data to the FICS server 202. This verification, whether completed locally or at the FICS server, can help to ensure the integrity of patient-specific data prior to transmission to the FICS server 202 for conversion and storage in medical databases.

If sufficiency threshold for EHR is satisfied, the FICS server may generate, based on the patient-specific data for each of the plurality of patients, an update to a respective patient-specific EHR for each of the plurality of patients (block 508). For example, the patient may be identified from the submitted patient-specific raw data (e.g., via the FICS server 202 retrieving the patient profile 212 associated with the patient), and any existing EHR files associated with the patient can be retrieved. In some aspects, a new EHR file may be created for the patient based on the received patient-specific data.

At block 510, the FICS server may generate, based on the patient-specific EHR for each of the plurality of patients, a patient-specific electronic data capture (EDC) data associated with each of the plurality of patients.

The FICS server may determine whether there is correspondence (e.g., consistency) between the terms of EHR and EDC associated with each patient (block 512). In some aspects, this determination may be periodic (e.g., at refresh intervals) as part of the FICS server routinely checking for consistency of data stored across various medical databases.

If there is no correspondence, the FICS server may prompt an update to patient-specific EDC data (block 514). For example, the FICS server may notify, via the FICS app, the user that may have previously entered patient-specific EDC data of missing fields. The missing fields may be identified by the FICS server by searching through a list of forms that patient-specific data can be used to populate (e.g., EDC data used in various clinical research forms) and identify any data fields with insufficient or lack of entry.

If the correspondence is met, and/or after an update to patient-specific EDC data has been prompted, the FICS server may aggregate, in one or more of the plurality of electronic data management systems, a plurality of patient-specific EDC data associated with the plurality of patients (block 516). Electronic data management systems may include, but are not limited to EDC servers 258, the clinical trial management system 266, clinical data management system 274, and other data management systems 282.

Furthermore, at predetermined refresh intervals, the FICS server may update each of the plurality of electronic data management systems to store the plurality of patient-specific EDC data associated with the plurality of patients (block 518). For example, the FICS server may routinely compare patient-specific data stored in each of the electronic data management systems and check to see if the patient-specific data is consistent, even if the format, syntax, or structure of the patient-specific data as it is stored may vary between each electronic data management system.

Relaying Patient-Specific Data

Figure 6:
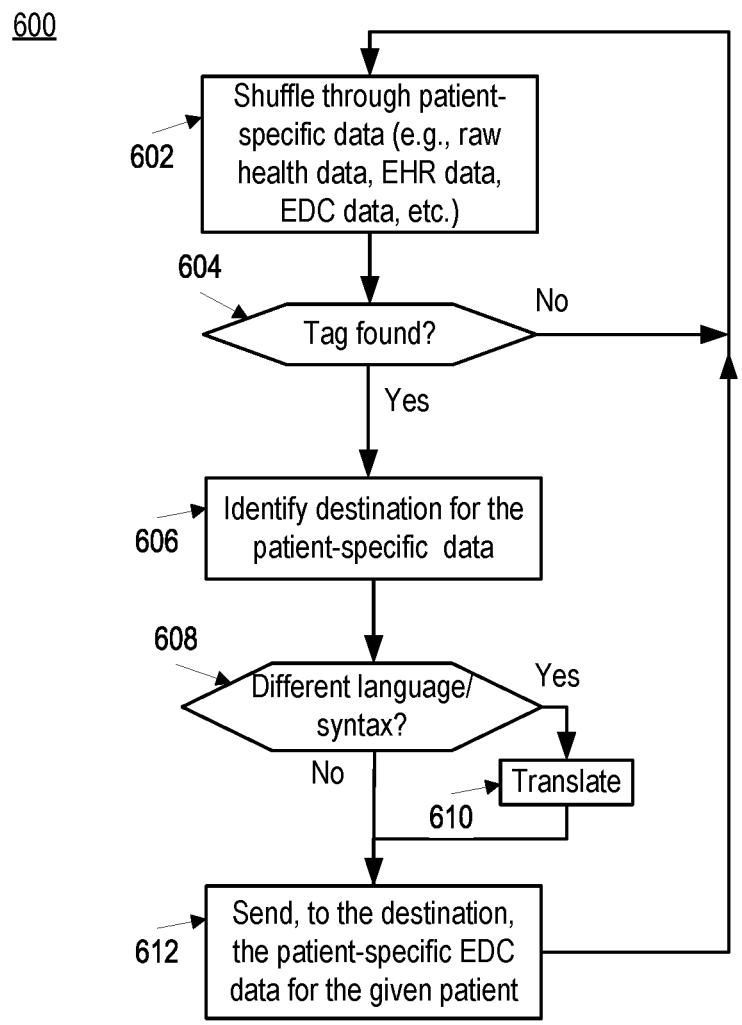
FIG. 6 illustrates a flow diagram of an example method of relaying patient-specific data using an interoperable platform for reducing redundancy in medical database management, according to an example embodiment of the present disclosure.

FIG. 6 illustrates a flow diagram of an example method 600 of relaying patient-specific data using an interoperable platform for reducing redundancy in medical database management, according to an example embodiment of the present disclosure. Specifically, one or more steps of method 600 may be performed once the FICS server has received and stored patient-specific data, and is determining whether and how to convert, reformat, transfer, and relay patient-specific data to another computing system in the network of computing systems involved in medical data management. One or more steps of method 600 may be performed by processor 230 of FICS server 202, e.g., based on instructions stored in memory 232, and based on information received via applications (FICS apps) running on various other devices and computing systems.

As part of a routine process, the FICS server may shuffle through patient-specific data (block 602). In some aspects, this step may occur as patient-specific data is generated. For example, patient-specific data may be generated as raw data entered via source devices 242, or may be generated after auto population by the FICS server into specific forms (e.g., EHR, EDC data, etc.) using the raw data. Also or alternatively, the FICS server may routinely retrieve patient-specific data for each patient, e.g., from stored databases of the electronic data management systems.

For each patient-specific data, the FICS server may determine whether there any tags (block 604). As previously discussed, the tag may be a form of metadata (e.g., generated by tag generator 226) that may indicate one or more characteristics of a received patient-specific data, such as an intended destination. Thus, if a tag is found, the FICS server may identify the destination for the patient-specific EDC data (block 606). The destination may include, for example, a certain CDMS, a certain CTMS, another electronic data management system (e.g., billing and financial computing system), etc. Furthermore, details regarding the destination may be looked up, including, for example, the network address and the desired or required form, format, syntax, or structure for patient-specific data.

The FICS server may determine whether the identified destination requires a different syntax or structure for presenting the patient-specific data (block 608). For example, the specific destination may customarily use specific forms and data fields to analyze patient-specific data, and may thus require patient-specific data to be filled into such forms. As used herein, a form may refer to the structure, format, and types of data fields for a desired or required presentation or patient-specific data by a specific computing system. Form may also include the desired or required language or vocabulary to be used for the entry of data in those data fields. Thus, the FICS server may determine whether the patient-specific data that is has received is in a different form from the form that is required by the destination system.

If there is a different form, the FICS server may translate the patient-specific data from its earlier form to the form required by the destination system (block 610). As used herein, a translation or a conversion may include a transformation of the presentation of patient-specific data from a previous form to a new form, including the transfer of patient-specific data from the structures, formats, and types of data fields of the previous form to the structures, formats, and types of data fields of the new form, and any changes in language or vocabulary of terms used in the patient-specific data. If the form is determined to not be different at block 608, the FICS server may send, to the destination system, the patient-specific data for the given patient (block 612). Alternatively, after patient-specific data has been translated in block 610, the FICS server may send the translated patient-specific data to the destination system.

Figure 7:
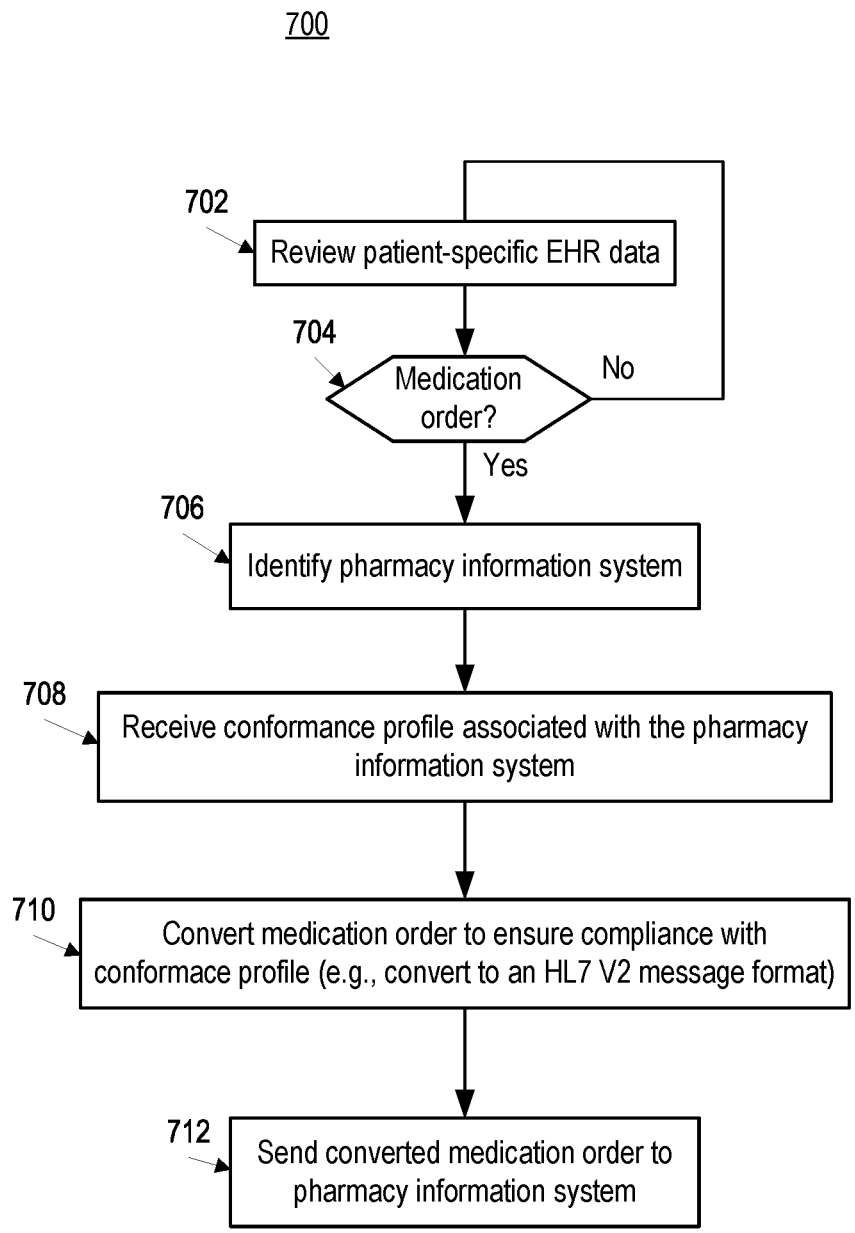
FIG. 7 illustrates a flow diagram of an example method of relaying patient-specific data involving a medication using an interoperable platform for reducing redundancy in medical database management, according to an example embodiment of the present disclosure.

FIG. 7 illustrates a flow diagram of an example method 700 of relaying patient-specific data involving a medication using an interoperable platform for reducing redundancy in medical database management, according to an example embodiment of the present disclosure. Moreover, method 700 may provide a more specific example of implementing method 600 in the context of relaying patient-specific data concerning a medication to a pharmacy information system. One or more steps of method 700 may be performed by processor 230 of FICS server 202, e.g., based on instructions stored in memory 232, and based on information received via applications (FICS apps) running on various other devices and computing systems.

At block 702, the FICS server may review patient-specific EHR data. For example, patient-specific EHR data may be reviewed as part of shuffling through patient-specific data for each patient, e.g., as part of step 602 in FIG. 6.

For a given patient-specific EHR data of a given patient, the FICS server may determine whether that patient-specific EHR data includes a medication order (block 704). For example, the FICS server may look for tags within the EHR data that indicate medication. In some aspects, the FICS server may identify terms associated with medicines, based on a repository of EHR terms 218 stored in mapping module 214. If no medication order is identified, the FICS server may continue reviewing other patient-specific EHR data for the given and remaining patients.

If the medication order is identified, the FICS server may identify a pharmacy information system (block 706). For example, the FICS server may identify the original sender of the patient-specific EHR data (e.g., the hospital information system 248 and/or source device 242), and then locate pharmacy information systems associated with the original sender (e.g., a pharmacy connected to the hospital). Also or alternatively, the FICS server may review the patient profile 212 of the patient associated with the EHR data, identify a pharmacy that the patient may have designated, and then determine the pharmacy information system associated with the pharmacy.

The FICS server may then receive a conformance profile associated with the pharmacy information system (block 708). The conformance profile may comprise an a priori agreement between an electronic health record system and destination system (e.g., the pharmacy information system). Moreover the conformance profiles, which may be stored for each destination system, may set forth the form requirements of messages (e.g., patient-specific data), for the messages to be accepted by the destination system. For example, pharmacy information systems often require an HL7 V2 message format for the transmission of appropriate information necessary to carry out a process, such as ordering a medication.

Thus, the medication order may be converted to ensure compliance with the conformance profile (block 710). For example, like block 610 in FIG. 6, the FICS server may translate and/or convert the medication order from its previous form (e.g., as a data field within the patient-specific EHR) to a form compliant with the conformance profile (e.g., an HL7 V2 message format).

The FICS server may then send the converted medication order to the pharmacy information system. For example, the FICS server may access the network address associated with the pharmacy information system identified in 706 and send the medication order via communication network 240 using network interface 234.

Leveraging the Interoperable Platform for Clinical Trials

Figure 8:
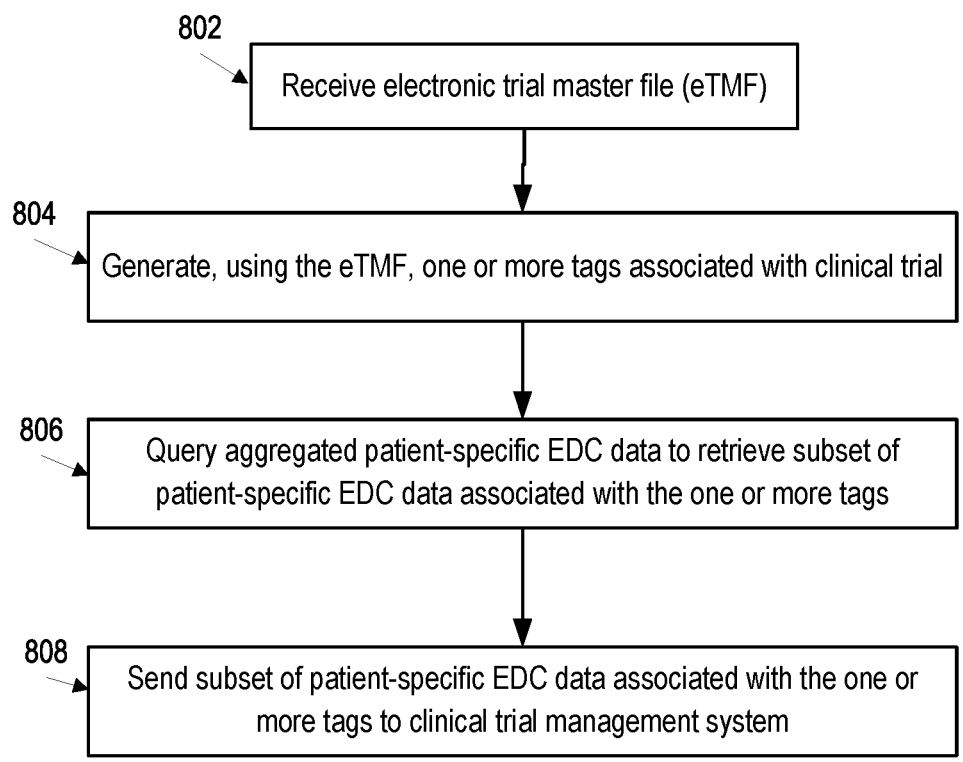
FIG. 8 illustrates a flow diagram of an example method of relaying clinical trial data using an interoperable platform for reducing redundancy in medical database management, according to an example embodiment of the present disclosure.

FIG. 8 illustrates a flow diagram of an example method 800 of relaying clinical trial data using an interoperable platform for reducing redundancy in medical database management, according to an example embodiment of the present disclosure. One or more steps of method 800 may be performed by processor 230 of FICS server 202, e.g., based on instructions stored in memory 232, and based on information received via applications (FICS apps) running on various other devices and computing systems.

At block 802, the FICS server may receive an electronic trial master file (eTMF). The eTMF may comprise essential clinical trial documents, images and other digital content in compliance with applicable regulatory requirements. In some aspects, a subset of files associated with a clinical trial may be received, instead of the entirety of the eTMF. For example, a researcher may wish to leverage the systems and methods presented herein to obtain large volume of patient-specific data for a clinical trial. The researcher may request, e.g., via FICS app 270 of CTMS 266, for any patient-specific data relevant for the clinical trial, and may be prompted to submit the eTMF or files of the eTMF for the FICS server to identify relevant terms for tag generation.

Using the eTMF or subset of the eTMF, one or more tags associated with the clinical trial may be generated (e.g., block 804). For example, the eTMF may be scanned for relevant clinical terms (e.g., specific diseases, specific medicines, specific treatment plans, etc.) and tags may be generated for those relevant clinical terms (e.g., via tag generator 226).

The FICS server may query aggregated patient-specific EDC data to retrieve a subset of patient-specific EDC data associated with the one or more tags. For example, FICS server may send query requests to EDC servers 258 for all stored patient-specific EDC data having the generated tags. In some aspects, the tags may comprise terms that may appear within the patient-specific EDC data (e.g., when decoded from encryption). The EDC servers 258 may then send (e.g., as a copy) a subset of its stored patient-specific EDC data, the subset having or being associated with the one or more tags.

The FICS server may then send the subset of patient-specific EDC data associated with the one or more tags to the clinical trial management system (block 808). Method 800 may occur in a gradual basis, e.g., as new patient-specific data is received, generated into patient-specific EDC data, stored in the EDC servers 258, and periodically queried by the FICS server. In some embodiments, the patient-specific EDC data may be ranked or otherwise categorized in relevance, e.g., based on how closely associated the patient-specific EDC data may be to the one or more tags associated with the clinical trial.

It will be appreciated that all of the disclosed methods and procedures described herein can be implemented using one or more computer programs or components. These components may be provided as a series of computer instructions on any conventional computer readable medium or machine-readable medium, including volatile or non-volatile memory, such as RAM, ROM, flash memory, magnetic or optical disks, optical memory, or other storage media. The instructions may be provided as software or firmware, and/or may be implemented in whole or in part in hardware components such as ASICs, FPGAs, DSPs or any other similar devices. The instructions may be configured to be executed by one or more processors, which when executing the series of computer instructions, performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method for reducing redundancy in medical database management, the method comprising:
generating, by a tag generator of a computing system having one or more processors, one or more tags for each of a plurality of patient-specific electronic data capture (EDC) data, the one or more tags for each patient-specific EDC data corresponding to metadata stored in the respective patient-specific EDC data indicating one or more characteristics of the respective patient-specific EDC data;
receiving, by the computing system, via a cloud-native and web-based application, a request for a subset of the plurality of patient-specific EDC data, wherein the cloud-native and web-based application is managed by an interoperable application programming interface (API) of the computing system and accessible to a plurality of source devices, a plurality of hospital information systems, and a plurality of electronic data management systems;
identifying, by the computing system, based on a first tag of the one or more tags associated with the subset of the plurality of patient-specific EDC data and identified by the request, a destination system for the subset of the plurality of patient-specific EDC data,
wherein the subset of the plurality of patient-specific EDC data is automatically generated from a subset of a plurality of patient-specific electronic health records (EHRs) and available for identification prior to receiving the request; and
sending, to the destination system and in response to the request, the subset of the plurality of patient-specific EDC data.

2. The method of claim 1, further comprising:
identifying, via a source verification unit of the interoperable API, a source of the request for the subset of the plurality of patient-specific EDC data, wherein the source is one of the source devices, hospital information systems, or the electronic data management systems; and
providing, to the source, via the cloud-native and web-based application, access to the subset of the plurality of patient-specific EDC data.

3. The method of claim 1, further comprising, prior to receiving the request,
for each of a plurality of hospital information systems, for each of a plurality of source devices associated with the plurality of hospital information systems, and for each of a plurality of patients,
receiving, by the computing system from a given source device associated with a given hospital information system, patient-specific health data for a given patient; and generating, by a mapping module of the computing system, and based on the patient-specific health data, a patient-specific EDC data associated with the given patient; and aggregating, in a first electronic data management system of a plurality of electronic data management systems, the plurality of patient-specific EDC data associated with the plurality of patients.

4. The method of claim 3, wherein generating the patient-specific EDC data associated with the given patient comprises:

generating, by the mapping module and based on the patient-specific health data, an update to a patient-specific electronic health record (EHR) for the given patient; and generating, by the mapping module and based on the patient-specific EHR, the patient-specific EDC data associated with the given patient.

5. The method of claim 3, further comprising:

updating, by the computing system and at predetermined refresh intervals, each of the plurality of electronic data management systems to store the plurality of patient-specific EDC data associated with the plurality of patients.

6. The method of claim 3, wherein generating the patient-specific EDC data comprises:

mapping lexical tokens between a dictionary associated with the given hospital information system and a dictionary associated with the first electronic data management system.

7. The method of claim 1, further comprising:

automatically sending, by the computing system and based on a second tag associated with a second subset of the plurality of patient-specific EDC data, the second subset of the plurality of patient-specific EDC data to a second destination system.

8. The method of claim 7, wherein the second tag indicates that the second subset of the plurality of patient-specific EDC data is a medication order, the method further comprising:

identifying, based on the medication order, a pharmacy information system as the second destination system.

9. The method of claim 8, further comprising:

receiving a conformance profile associated with the pharmacy information system; and converting, based on the conformance profile, the second subset of the plurality of patient-specific EDC data to a message format in compliance with the conformance profile.

10. One or more non-transitory computer readable media storing instructions that, when executed by one or more processors, cause the one or more processors to perform a method comprising:

generating, by a tag generator of a computing system having one or more processors, one or more tags for each of a plurality of patient-specific electronic data capture (EDC) data, the one or more tags for each patient-specific EDC data corresponding to metadata stored in the respective patient-specific EDC data indicating one or more characteristics of the respective patient-specific EDC data;

receiving, by the computing system, via a cloud-native and web-based application, a request for a subset of the plurality of patient-specific EDC data, wherein the cloud-native and web-based application is managed by an interoperable application programming interface (API) of the computing system and accessible to a plurality of source devices, a plurality of hospital information systems, and a plurality of electronic data management systems;

identifying, by the computing system and based on a first tag of the one or more tags associated with the subset of the plurality of patient-specific EDC data and identified by the request, a destination system for the subset of the plurality of patient-specific EDC data, wherein the subset of the plurality of patient-specific EDC data is automatically generated from a subset of a plurality of patient-specific electronic health records (EHRs) and available for identification prior to receiving the request; and sending, to the destination system and in response to the request, the subset of the plurality of patient-specific EDC data.

11. The non-transitory computer readable media of claim 10, the method further comprising:

identifying, via a source verification unit of the interoperable API, a source of the request for the subset of the plurality of patient-specific EDC data, wherein the source is one of the source devices, hospital information systems, or the electronic data management systems; and providing, to the source, via the cloud-native and web-based application, access to the subset of the plurality of patient-specific EDC data.

12. The non-transitory computer readable media of claim 10, the method further comprising, prior to receiving the request:

for each of a plurality of hospital information systems, for each of a plurality of source devices associated with the plurality of hospital information systems, and for each of a plurality of patients, receiving, by the computing system from a given source device associated with a given hospital information system, patient-specific health data for a given patient; and generating, by a mapping module of the computing system, and based on the patient-specific health data, a patient-specific EDC data associated with the given patient; and aggregating, in a first electronic data management system of a plurality of electronic data management systems, the plurality of patient-specific EDC data associated with the plurality of patients.

13. The non-transitory computer readable media of claim 12, wherein generating the patient-specific EDC data associated with the given patient comprises:

generating, by the mapping module and based on the patient-specific health data, an update to a patient-specific electronic health record (EHR) for the given patient; and generating, by the mapping module and based on the patient-specific EHR, the patient-specific EDC data associated with the given patient.

14. The non-transitory computer readable media of claim 12, the method further comprising:

updating, by the computing system and at predetermined refresh intervals, each of the plurality of electronic data management systems to store the plurality of patient-specific EDC data associated with the plurality of patients.

15. The non-transitory computer readable media of claim 12, wherein generating the patient-specific EDC data associated with the given patient comprises:

mapping lexical tokens between a dictionary associated with the given hospital information system and a dictionary associated with the first electronic data management system.

16. The non-transitory computer readable media of claim 10, the method further comprising:
automatically sending, by the computing system and based on a second tag associated with a second subset of the plurality of patient-specific EDC data, the second subset of the plurality of patient-specific EDC data to a second destination system.

17. The non-transitory computer readable media of claim 16, wherein the second tag indicates that the second subset of the plurality of patient-specific EDC data is a medication order, the method further comprising:
identifying, based on the medication order, a pharmacy information system as the second destination system.

18. The non-transitory computer readable media of claim 17, the method further comprising:
receiving a conformance profile associated with the pharmacy information system; and
converting, based on the conformance profile, the second subset of the plurality of patient-specific EDC data to a message format in compliance with the conformance profile.

19. A system for reducing redundancy in medical database management, the system comprising:
an interoperable application program interface (API) for reducing redundancy in medical database management and communicatively managing a cloud-native and web-based application accessible to each of: a plurality of hospital information systems, a plurality of source devices associated with each of the plurality of hospital information systems, and a plurality of electronic data management systems;
a tag generator;
one or more processors; and
memory storing instructions that, when executed by the one or more processors, cause the one or more processors to:
generate, by the tag generator, one or more tags for each of a plurality of patient-specific electronic data capture (EDC) data, the one or more tags for each patient-specific EDC data corresponding to metadata stored in the respective patient-specific EDC data indicating one or more characteristics of the respective patient-specific EDC data;
receive, via the cloud-native and web-based application, a request for a subset of the plurality of patient-specific EDC data;
identify, based on a first tag of the one or more tags associated with the subset of the plurality of patient-specific EDC data and identified by the request, a destination system for the subset of the plurality of patient-specific EDC data,
wherein the subset of the plurality of patient-specific EDC data is automatically generated from a subset of a plurality of patient-specific electronic health records (EHRs) and available for identification prior to receiving the request; and
send, to the destination system and in response to the request, the subset of the plurality of patient-specific EDC data.

20. The system of claim 19, wherein the instructions, when executed by the one or more processors, cause the one or more processors to:
automatically send, based on a second tag associated with a second subset of the plurality of patient-specific EDC data, the second subset of the plurality of patient-specific EDC data to a pharmacy information system, wherein the second tag indicates that the second subset of the plurality of patient-specific EDC data is a medication order.

* * * * *